United States Patent [19]

Montgomery et al.

[11] Patent Number: 4,766,005

[45] Date of Patent: Aug. 23, 1988

[54] MATERIAL AND METHOD FOR OBTAINING STRONG ADHESIVE BONDING TO PROTEINACEOUS SUBSTRATES

[75] Inventors: Robert E. Montgomery, Los Angeles; George W. Schaeffer, Sherman Oaks, both of Calif.

[73] Assignee: OPI Products, Inc., North Hollywood, Calif.

[21] Appl. No.: 924,896

[22] Filed: Oct. 30, 1986

[51] Int. Cl.$^4$ .................. A61K 7/04; A61K 7/06; A01G 5/06
[52] U.S. Cl. ............................... 427/4; 424/61; 424/70; 427/323
[58] Field of Search .................. 424/25, 31, 32, 33, 424/61, 70; 427/4, 323

[56] References Cited

U.S. PATENT DOCUMENTS 4,547,363 10/1985 Joos .................................. 424/61

Primary Examiner—Michael Lusignan
Attorney, Agent, or Firm—Blakely, Sokoloff, Taylor, Zafman

[57] ABSTRACT

This invention relates to materials and methods for obtaining strong adhesive bonds of coatings, composites and adhesives to proteinaceous substrates consisting either entirely, or in part of keratin, are disclosed. The invented materials comprise a non-aqueous solvent capable of adjusting the pH of the surface of the substrate to a pH of 8.0 or greater. The invented method comprises treating the substrate with the invented material until the pH of the surface is in the range of pH 9.0 to 11.0, followed by bonding a coating, composite or adhesive thereto.

12 Claims, No Drawings

MATERIAL AND METHOD FOR OBTAINING STRONG ADHESIVE BONDING TO PROTEINACEOUS SUBSTRATES

FIELD OF THE INVENTION

This invention relates to materials and methods for obtaining strong adhesive bonds of coatings, composites and adhesives to proteinaceous substrates. More particularly, strong adhesive bonds between coatings, composites and adhesive compositions, on the one hand and proteinaceous substrates, such as human fingernails and toe nails, and the hooves of horses, on the other hand are disclosed which are particularly useful in such areas as artificial fingernail prosthesis in the cosmetic field and filling and sealing materials for hoof bonding in the area of veterinary practice.

BACKGROUND OF THE PRIOR ART

The reparation, adornment, and prosthetic extension of keratinaceous structures, namely, human fingernails and toe nails and livestock hoofs, has been a common practice for centuries. Fingernails are currently known to be coated with multicolored nitrocellulose lacquers, repaired with cyanoacrylate adhesives, and extended with the use of acrylic monomer and polymer slurries or doughs that cure by peroxide/amine free radical mechanisms. Although the nitrocellulose lacquers and the cyanoacylate adhesives are relatively adherent to a fingernail plate, the acrylic materials employed for the purpose of creating an artificial fingernail prosthesis are not. Only after treatment of the fingernail surface with an unsaturated carboxylic acid, such as methacrylic acid (current commercial embodiments contain in excess of 70 percent methacrylic acid), will such acrylic monomer and polymer slurries or doughs adhere to the nail plate. Such harsh treatment on a relatively fragile surface poses a serious toxicological hazard due to the corrosive nature of these unsaturated carboxylic acids. Other unsaturated carboxylic acids presently being used in the described applications include either alone or in part, acrylic acid and beta-carboxyethyl acrylate. Lower concentrations of these unsaturated acids pose a decreased danger to the intact fingernail surface; however, at such lower concentrations the adhesion of the acrylic monomer and polymer slurry is minimized or lost completely. An analagous situation exists when attempting to repair a split or fractured hoof in that without the application of the corrosive and possibly toxic levels of unsaturated acids, very poor adhesion results.

Currently, the only known and readily practiced method for obtaining adhesion of prosthetic materials to wholly proteinaceous substrates, such as fingernails and hooves, has been the physical abrasion and roughening of the proteinaceous substrate surface with a file, sandpaper-like, or other abrasive material, followed by the application of unsaturated carboxylic acid solutions (in the artificial fingernail art known as primers), followed lastly by the application of the prosthetic material. The prosthetic material is not inherently to proteinaceous substrates. Rather, the prosthetic material also contains unsaturated groups, which, when cured, chemically bind with the unsaturated groups of the carboxylic acid solution applied to the proteinaceous substrate. Thus, an adhesive bond between said substrate and the prosthesis is provided.

The disadvantages of such a method and materials used in the prior art are as follows:

(1) too much physical abrasion or roughening of the proteinaceous substrate, particularly a living fingernail, can be harmful to the individual;

(2) in the area of hoof binding, cracks and fissures in the hooves are not readily abraded or roughened due to the inaccessability of the surface to such abrasive materials and methods;

(3) the unsaturated carboxylic acids that are often used (acrylic acid and methacrylic acid, either alone at full concentration or in combination with other diluents, are highly corrosive and can severely damage the protein of a fingernail or hoof or the underlying or surrounding living tissue; and (4) even with such harsh surface preparation as described above, the adhesive bonds obtained with such methods are poor and all too often inadequate to retain the prosthetic for sufficient periods of time or under stress, thus causing the prosthetic to break off in whole or in part.

SUMMARY OF THE PRESENT INVENTION

The present invention comprises materials and methods which both appreciably increase the adhesive bond strength of a coating, composite or adhesive to a proteinaceous substrate, while simultaneously decreasing the potential for physical or chemical harm to a living proteinaceous substrate.

What has been discovered is that the pretreatment of a keratinaceous substrate with a water-miscible, aprotic solvent that has been pH adjusted towards the alkali will result in stronger adhesion of coatings, composites, and adhesives to such a substrate than that adhesive strength observed under the same conditions to an untreated substrate. The crucial parameter resulting from such pretreatment has been observed to be a keratinaceous substrate surface pH of about 8.0 or greater and, preferably from about pH 10.0 to 11.0.

Briefly, the invention is accomplished by applying a nonaqueous solvent, preferably aprotic and of a low order of toxicity (if it is to be contacted with a proteinaceous substrate in vivo) that has been pH adjusted towards the alkali. Such a solution, when contacted with said proteinaceous substrate, is preferably of sufficient volatility and high purity, so that it evaporates rapidly, leaving substantially no residue. The proteinaceous substrate, after contact with and evaporation of the above solution, when contacted with a flat surface pH electrode, will register a pH reading of 8.0 or greater pH units, and preferably from 10.0 to 11.0 pH units. The treated proteinaceous substrate can then be contacted with any of a variety of one or more coatings, composites or adhesive compositions, which, as is the purpose of this invention, will adhere with equal to or better tensile bond strength than other harsher and potentially harmful methods and/or compositions.

The method of this invention consists generally of the following:

(1) Application of the pH-adjusting solvent or solution to the proteinaceous substrate; then (2) Optionally applying an adhesion promoting agent to optimize the bond between the proteinaceous substrate and the adhesive, coating or composite; and finally, (3) Applying and curing the adhesive, coating or composite to achieve a desired result such as fingernail extension or coating, or hoof repair or bonding.

In the preferred embodiment of this invention, the proteinaceous substrate is contacted, through the use of a brush, or spray-on method or the like, with a solution of anhydrous ethyl acetate that has been pH adjusted towards the alkali with a small amount of aqueous ammonium hydroxide. After evaporation of such a solution at ambient temperature, the surface of the proteinaceous substrate, when tested for surface pH with a flat-surface pH electrode, will typically register a pH reading of approximately 9.0 to 11.0, depending upon the length of solution contact time, amount of ammonium hydroxide added, and the volume of solution applied to the substrate. The proteinaceous substrate may then be optionally contacted with an adhesion-promoting agent that can further improve the bond strength between the coating, composite or adhesive and the proteinaceous substrate. Such adhesion promoting agents demonstrate improved properties when comparing their use on pH adjusted proteinaceous surfaces versus non-pH adjusted proteinaceous surfaces.

Application of the pH adjusted solvents of this invention is preferably by either a brush or spray-on method. The keratinaceous substrate may be roughened by use of any standard abrasive material or substance, such as an emery board or file to increase the available surface area for obtaining higher bond strengths; however, this procedure is not critical to the practice of this invention. In fact, the currect practice of fingernail surface abrasion prior to prosthetic fingernail attachment can be harmful to the individual's nail and is not recommended. Abrasion of hoofs, when practical, can help to achieve optimal bond strengths, but again, is not required.

DETAILED DESCRIPTION

In a living organism, keratinaceous structures are derived from ectodermal (skin) cells and generally have little or no vascularization. A variety of alpha keratins have been isolated with variations in their amino acid makeup; however, keratins found in analagous anatomical structures (for example, fingernails and hoofs, or hair and wool) are generally composed of proteins having very similar amino acid profiles.

Although the types of substrates, namely proteinaceous substrates, and, more specifically, those proteinaceous substrates comprising either wholly or in part of keratin, are limited in number, the method and materials of this invention are of significant commercial and toxicological importance. The two primary fields of practice of this invention are related to adhering artificial fingernail prostheses or fingernail polish to natural fingernail plates and adhering hoof mending compositions to cracked or split hooves in livestock. Both of these substrates are comprised almost entirely of keratin, a water-insoluble, fibrous protein that is a major structural component of skin, hair, wool, scales, feathers, quills, nails, hoofs, horns, and silk. More specifically, the class of keratins known as "alpha" keratin, which are characterized by a relatively large amount of the amino acid cystine are the major consituents of nails and hoofs. It is these alpha keratin substrates which are primarily involved in the practice of this invention.

In general, the method of this invention can be accomplished by contacting a proteinaceous substrate, such as a keratin fingernail or horse or cattle hoof, with a water-miscible, preferably aprotic solvent that has been pH adjusted towards the alkali. Such pH adjustment is accomplished most easily by the addition of small quantities of aqueous ammonium hydroxide, or morpholine, but may alternatively include, either alone or in part, a variety of amines, such a N-methyl pyrollidone, N,N-dimethylaminoethyl methacrylate, triethylamine, triethanolamine, and other primary, secondary or tertiary amines, either saturated or unsaturated, as described in more detail below. Treatment of the proteinaceous surface to obtain the desired pH in the range of from about 8.0 to about 12.0 or possibly higher is the crucial parameter in the practice of this invention.

The method of this invention consists of the following steps:

(1) Application of the pH-adjusting solvent or solution to the proteinaceous substrate; then (2) Optionally applying an adhesion promoting agent to optimize the bond between the proteinaceous substrate and the adhesive, coating or composite; and finally, (3) Applying and curing the adhesive, coating or composite to achieve a desired result such as fingernail extension or hoof repair or bonding.

Solvents or combinations of solvents to be employed in this invention should be miscible with water and aprotic, although combinations of water-miscible and non-water-miscible solvents may be utilized in many instances. The term miscible, as used herein, means that the solubility of water in the solvent at 25° C. is at least 5% w/w. Also, as will be shown, decreased bond strengths are obtained with solvents that possess active hydrogen atoms, otherwise known as protic solvents. An example of such a protic solvent is isopropyl alcohol.

For compositions for use on human fingernails, the solvent choice should be limited to those that ar cosmetically and toxicologically acceptable. The most preferred solvents of this invention are capable of forming an azeotrope, (that is, a mixture of two or more substances, generally liquids, that evaporate or boil off as a vapor having the same composition as the original liquid) with water, are aprotic, and are low in toxicity. The latter characteristic is especially important in the applications of this invention involving human contact. The most preferred solvents are ethyl acetate, butyl acetate, acetonitrile, and trichloroethylene. Other solvents that can be employed alone, or in combination with each other or the above preferred solvents are acetone, cyclohexane, n-hexane, trichloroethylene, methyl ethyl ketone, N-methyl pyrrolidone, dimethyl sulfoxide, dimethyl formamide, diethylene glycol dimethyl ether, and tetrahydrofuran. In addition, small amounts (less than 20 to 30 percent) of water-miscible or non-water-miscible protic solvents can be employed without significantly decreasing the effectiveness of the present invention. Solvents in this group include isopropanol, ethanol, butanol, amyl alcohol, n-propanol, and any other low toxicity primary, secondary or tertiary aliphatic or aromatic alcohols. Also of some utility in the compositions of this invention are butyrolactone and valerolactone.

The pH adjustment of the above solvent or solvent mixture is most easily accomplished by the addition of small amounts of ammonium hydroxide, generally in the range of from about 0.01 percent weight to about 10 percent by weight. Although ammonium hydroxide is the most preferred alkalizing agent due to its volatility and relatively innocuous nature in the compositions of this invention, a number of other compounds can be used alone or in combination with ammonium hydroxide to accomplish the desired pH adjustment of the proteinaceous substrate. In general, the class of compounds including primary, secondary and tertiary amines are suitable for this purpose, namely of shifting the pH of the proteinaceous substrate to between about 8.0 and about 12.0. Suitable amines include morpholine, N-methyl pyrollidone, dimethylaminoethyl methacrylate, triethylamine, dimethylaminoethanol, and others. Also contemplated in the practice of this invention are inorganic alkalizing agents such as sodium hydroxide, potassium hydroxide, calcium hydroxide, zinc hydroxide, and others. Alkanolamines, such as triethanolamine, should be kept at a minimum concentration due to their active hydrogens which can interfere with adhesion of a coating, composite, or adhesive to a keratinaceous substrate.

Adjustment of the pH of the solvent or solvent mixture is accomplished most readily by the addition of small quantities (less than 1% w/w) of 28-30% ammonium hydroxide. However, small quantities of a variety of primary, secondary and tertiary amines may be added, either alone, in combination, or in combination with ammonium hyrdroxide.

After the keratinaceous substrate is treated with the solvent in a sufficient quantity and for a sufficient time to increase the pH of the surface of the substrate to the desired range, a variety of adhesion promoting agents may be applied. Since the pH adjustment is towards the alkali resulting in a proteinaceous surface pH of approximately 9.0 to 11.0, adhesion promoting agents containing carboxylic (-COOH) groups have demonstrated the best adhesive properties. A wide variety of carboxylic acid group-containing adhesion promoters were observed to be successful. Again, the adhesion promotion observed employing any particular adhesion promoting agent was always greater on the pH-adjusted proteinaceous substrate as compared with the non-pH-adjusted proteinaceous substrate.

The following adhesion promoting agents have been utilized either at full strength, diluted in appropriate carrier solvents, or where the adhesion promoting agent is a solid, dissolved in solution. Aqueous, non-aqueous and emulsion carriers have been employed and/or are contemplated. Monomeric unsaturated species for adhesion promotion include methacrylic acid, acrylic acid, beta-carboxyethyl/acrylate, itaconic acid, maleic acid, fumaric acid, pyromellitic dianhydride diacrylate and dimethacrylate and 4 - methacryloxyethyl trimellitic dianhydride diacrylate and dimethacrylate. The anhydrides of methacrylic acid, itaconic acid, and maleic acid are also observed to provide improvement in adhesion of unsaturated adhesives, coatings and composites. Higher molecular weight adhesion promoting agents include poly(vinylpyrrolidone), poly(vinyl pyrrolidone-co-dimethylaminoethyl methacrylate, poly(acrylate-co-acrylic acid), polyacrylic acid, poly(methyl vinyl ether-co-maleic anhydride), in addition to acrylated urethanes, acrylated and methacrylated epoxies, and acrylated and methacrylated polyesters. Hydroxyethyl methacrylate and acrylate adducts of polymeric anhydrides and co-anhydrides (such as polymethacrylic acid anhydride and poly(methyl vinyl ether-co-maleic anhydride) have been shown to be particularly useful in promoting adhesion of unsaturated adhesives and coatings to proteinaceous substrates. Any of the above compounds, alone or in combination, have demonstrated some degree of adhesion promotion of adhesives, coatings and/or composites to proteinaceous substrates, a property that is greatly enhanced by the pH adjustment step of this invention.

The exact nature of the pH criticality is not known, however without being bound to any particular theory, it can be conjectured that the pH shift towards the alkali tends to create a greater number and variety of charged nucleophilic amino acid side chains (such as $-NH_2$, $-COO^-$, and $S^-$) than would be present at neutral or acidic pH. Such nucleophiles, if present, may be more reactive with reactants in the coating, composite or adhesive in contact with the keratinaceous substrate, thus creating a stronger bond. The nature of these interactions is not known.

Since the pH adjusting solvent or solution is in liquid form, a wide variety of delivery systems are possible and contemplated. The solvent or solution can be placed in a bottle (which could have a brush built into the cap for application on the proteinaceous substrate), in spray or aerosol form, in a bottle, jar or can with submerged, single-use pads or sponges for application, or any number of other suitable delivery systems for liquid compositions. Attention should be paid to the container's material and construction, as some materials (such as glass) might show long term sensitivity to alkaline liquids of this sort.

EXAMPLE ONE

A solution was prepared containing 995 grams of anhydrous ethyl acetate and 5 grams of 30% ammonium hydroxide. The solution was packaged in one ounce glass bottles with brush caps for use in the tests of this example.

In order to determine the extent of adhesion improvement by the pH adjustment step of this invention, a suitable model for proteinaceous substrates, namely cattle hooves, was chosen. Adhesive strength of a cured adhesive, coating or composite was determined by utilizing flat, polished sections of cattle hooves, with the fibers of the hoof running parallel to the surface. The tensile load was determined by curing the adhesive, coating or composite on the surface of the hoof, and subjecting said material to a load increase of 250 psi/min by an Instron Tensile, Model TTCL (Instron Engineering Corp., Quincy, Mass.).

In each test below, a cattle hoof was brushed with the pH-adjusting solution of this Example and allowed to dry for one minute. Optionally, an adhesion promoter is applied at this point and allowed to dry. Finally, the following materials are admixed and immediately applied to the surface of the hoof.

| Part A | |
|---|---|
| Ethyl methacrylate | 2.225 grams |
| Diethylene glycol dimethacrylate | 0.250 grams |
| N,N—dihydroxyethyl-p-toluidine | 0.025 grams |
| Part B | |
| 70/30 Ethyl methacrylate/methyl methacrylate copolymer | 7.450 grams |
| Benzoyl peroxide | 0.050 grams |
| | 10.000 grams |

The above material comprised of Parts A and B is representative of a self-curing artificial fingernail composition in which Parts A and B are admixed to initiate a free-radical curing mechanism, resulting in a hard, durable polymer.

Table 1 lists the results of this Example

TABLE 1

| Test Number | pH Adjustment | Adhesion Promoter | Tensile Adhesive Strength (psi) |
|---|---|---|---|
| 1 | no | — | 380 |
| 2 | yes | — | 920 |
| 3 | nk$ | methacrylic acid (MAA) | 1,350 |
| 4 | yes | methacrylic acid | 1,975 |
| 5 | no | MAA/ethyl acetate 50:50 | 1,020 |
| 6 | yes | MAA/ethyl acetate 50:50 | 1,930 |
| 7 | no | ethyl acetate | 390 |
| 8 | yes | ethyl acetate | 905 |
| 9 | no | Polymer C (1%) in acetone | 1,185 |
| 10 | yes | Polymer C (1%) in acetone | 1,880 |
| 11 | no | Polymer D (.5%) in acetone | 1,260 |
| 12 | yes | Polymer D (.5%) in acetone | 2,095 |

MAA = methacrylic acid
Polymer C = poly(acrylate-co acrylic acid)
Polymer D = stoichiometric combination of hydroxyethyl methacrylate and methyl vinyl ether/maleic anhydride copolymer (Gantrez AN-119, GAF Corporation)

The above figures for tensile adhesive strength are the averages of five (5) trials, measured at 25° C. and 50 percent relative humidity.

Increases in the adhesive strength on the pH-adjusted substrates ranged from 46% to 142% improvement in the above series of tests. Drastic improvements of up to 551% (compare the tensile adhesion strength of test number 12 to test number 1) were observed in tests consisting of pH adjustment followed by application of an adhesion promoter, compared to no treatment at all.

EXAMPLE TWO

A number of different solvent systems were investigated as to their utility a carriers for the pH adjusting agents of the present invention. The following systems were prepared and tested, as in Example One, for their adhesion-promoting potential. The curable coating in this example was a hoof bonding agent that is cured with ultraviolet light. Exposure intensity was 7.0 mw/cm² and exposure time was kept constant for all samples at 300 seconds.

TABLE 2

| System | Composition | Wt. Percent | Tensile Adhesive Strength (psi) |
|---|---|---|---|
| A | Ethyl acetate | 99.5 | 1650 |
|   | Ammonium hydroxide | 0.5 |  |
|   |  | 100.0 |  |
| B | No treatment |  | 770 |
| C | Ethyl acetate | 49.75 | 1420 |
|   | Isopropanol | 49.75 |  |
|   | Ammonium hydroxide | 0.50 |  |
|   |  | 100.0 |  |
| D | Ethyl acetate | 100.00 | 845 |
| E | Trichloroethylene | 99.5 | 1555 |
|   | Ammonium hydroxide | 0.5 |  |
|   |  | 100.0 |  |
| F | Trichloroethylene | 99.5 | 1380 |
|   | Morpholine | 0.5 |  |
|   |  | 100.0 |  |
| G | Ethyl acetate | 98.0 | 1780 |
|   | Ammonium hydroxide | 2.0 |  |
|   |  | 100.0 |  |
| H | Ethyl acetate | 97.0 | 1950 |
|   | Ammonium hydroxide | 0.5 |  |
|   | Dimethylaminoethyl | 2.5 |  |

TABLE 2-continued

| System | Composition | Wt. Percent | Tensile Adhesive Strength (psi) |
|---|---|---|---|
|   | methacrylate | 100.0 |  |

It is anticipated that optionally applying an adhesion promoting agent after the pH adjustment step in the above example would significantly improve the tensile adhesive strength of the hoof bonding composition. However, as can be seen by the results above, the addition of an adhesion promoter is only optional; bond strengths of sufficiently high working strength are achieved with the pH adjusting compositions alone.

The compositions and methods having been described above, in general and in their preferred embodiments, it will be obvious to one of ordinary skill in the art that a number of modifications, additions and alterations can be made to the general formula without departing from the scop of the present invention.

We claim:
1. A method of treating proteinaceous substrates to obtain strong bonding of composites, coatings or adhesives thereto, comprising applying a pH adjustig material to said proteinaceous substrate to adjust the pH of said proteinaceous substrate to a pH of approximately 8.0 or greater, said pH adjusting material comprising:
   a major amount of a non-aqueous solvent selected from the group consisting of methyl lactate, isoamyl acetate, acetone, cyclohexane, n-hexane, trichloroethylene, methyl ethyl ketone, isopropanol, ethanol, butanol, amyl alcohol, n-propanol, primary, secondary or tertiary aliphatic or aromatic alocohols, butyrolactone, valerolactone and N-methyl pyrollidone, ethyl acetate butyl acetate, dimethyl sulfoxide, dimethyl formamide, diethylene glycol dimethyl ether and acetonitrile, or combinations thereof; and
   an effective amount of an alkalizing agent selected from the group consisting of ammonium hydroxide, morpholine, N-methyl pyrollidone, dimehtylaminethyl metacrylate, triethylamine, dimethylaminoethanol, sodium hydroxide, ptassium hydroxide, calcium hydroxide and zinc hydroxide.

2. The method of claim 1 wherein said solvent is selected from ethyl acetate, butyl acetate, acetonitrile and trichloroethylene.

3. The method of claim 1 wherein said solvent comprises approximately in the range of 0.01 to 10.0 weight percent ammonium hydroxide.

4. The method of claim 1 further comprising the step of contacting the pH adjusted proteinaceous substrate with an adhesion promoting agent comprising at least one reactive group selected from:

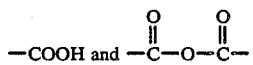

5. The method of claim 4 wherein said adhesion promoting agent is selected from the group consisting of unsaturated carboxylic acids, unsaturated carboxylic acid anydrides, polymeric carboxylic acids and polymeric carboxylic acid anhydrides.

6. The method of claim 5 wherein said adhesion promoting agent is selected form the group consisting of methacrylic acid, acrylic acid, beta-carboxyethylacrylate, itaconic acid, maleic acid, fumaric acid, pyromellitic dianhydride diacrylate and dimethacrylate, 4-metharyloxyethyl trimellitic dianhydride diarylate and dimethacrylate, anhydride derivatives of methacrylic acid, itaconic acid, maleic acid, poly(vinylpyrrolidione), poly (vinyl pyrrolidone-co-dimethylaminoethyl methacrylate), poly(acrylate-co-acrylic acid), polyacrylic acid, anhydride derivatives of polyacrylic acid and polymethacrylic acid, poly(methyl vinyl either-co-maleic anhydride) and hydroxyethyl methacrylate and acrylate adducts of polymeric anhydrides and co-anhydrides.

7. A composition for treating proteinaceous substrates to obtain strong bonding of coatings, composites or adhesives thereto consisting essentially of:
   a major amount of a non-aqueous solvent selected from the group consisting of methyl lactate, isoamyl acetate, acetone, cyclohexane, n-hexane, trichloroethylene, methyl ethyl ketone, isopropanol, ethanol, butanol, amyl alcohol, n-propanol, primary, secondary and tertiary aliphatic and aromatic alcohols, butyrolactone, valerolactone and N-methyl pyrollidone, ethyl acetate, butyl acetate, dimethyl sulfoxide, dimethyl formamide, diethylene glycol dimethyl ether and acetonitrile, and combinations thereof; and
   an effective amount of an alkalizing agent selected from the group consisting of ammonium hydroxide, morpholine, N-methyl pyrollidone, dimethylaminethyl methacrylate, triethylamine, dimethylamino-ethanol, dimethylaminoethanol, sodium hydroxide, potassium hydroxide, calcium hydroxide and zinc hydroxide, said alkalizing agent being provided in a sufficient amount to render said composition capable of adjusting the pH of a surface of said proteinanceous substrate to a pH of approximately 8.0 or greater.

8. The composition of claim 7 wherein said solvent is selected from ethyl acetate, butyl acetate, acetonitrile and trichloroethylene.

9. The composition of claim 7 wherein said solvent comprises approximately in the range of 0.01 to 10.0 weight percent ammonium hydroxide.

10. The composition of claim 9 wherein said solvent comprises less than 1.0 weight percent of 28 to 30% solution of ammonium hydroxide to adjust the pH of the surface of said proteinaceous substrate to a pH greater than 8.0.

11. A composition for treating proteinaceous substrates to obtain strong bonding of composites, coatings or adhesives thereto, consisting of approximately by weight:
   99% ethyl acetate,
   1% ammonium hydroxide (28% solution).

12. A method of treating proteinaceous substrate to obtain strong bonding consisting of:
   applying a pH adjusting material, said pH adjusting material consisting essentially of approximately by weight:
   99% ethyl acetate;
   1% ammonium hydroxide (28% solution);
   and applying an adhesion promoting agent selected from methacrylic acid, acrylic acid, betacarboxyethylate, itaconic acid, maleic acid, fumaric acid, pyromellitic dianhydride diacrylate and dimethacrylate 4-methacryloxyethyl, trimellitic dianhydride diacrylate and diemthacrylate, anhydride derivatives of methacrylic acid, itaconic acid, maleic acid, poly(vinylpyrrolidone), poly (vinyl pyrrolidone-co-dimethylaminoethyl methacrylate), poly(acrylate-coacrylic acid), polyacrylic acid, anhydride derivatives of polyacrylic acid and polymethacrylic acid, poly(methyl vinyl either-co-maleic anhydride) and hydroxyethyl methacrylate and acrylate adducts of polymeric anhydrides and co-anhydrides.

* * * * *